United States Patent
Hong et al.

(10) Patent No.: US 10,189,760 B2
(45) Date of Patent: Jan. 29, 2019

(54) METHOD FOR PREPARING SITAGLIPTIN INTERMEDIATE VIA ASYMMETRICAL REDUCTION METHOD

(71) Applicants: ZHEJIANG HUAHAI PHARMACEUTICAL CO., LTD., Linhai, Zhejiang (CN); SHANGHAI SYNCORES TECHNOLOGIES INC. LTD., Shanghai (CN)

(72) Inventors: Jian Hong, Shanghai (CN); Yusheng Wang, Shanghai (CN); Boyu Wang, Shanghai (CN); Luning Huang, Shanghai (CN); Eric Gu, Shanghai (CN)

(73) Assignees: ZHEJIANG HUAHAI PHARMACEUTICAL CO., LTD., Zhejiang (CN); SHANGHAI SYNCORES TECHNOLOGIES INC. LTD., Shanghai (CN)

( * ) Notice: Subject to any disclaimer, the term of this patent is extended or adjusted under 35 U.S.C. 154(b) by 0 days.

(21) Appl. No.: 15/319,370

(22) PCT Filed: Oct. 9, 2015

(86) PCT No.: PCT/CN2015/091539
§ 371 (c)(1),
(2) Date: Dec. 16, 2016

(87) PCT Pub. No.: WO2016/055015
PCT Pub. Date: Apr. 14, 2016

(65) Prior Publication Data
US 2017/0305822 A1    Oct. 26, 2017

(30) Foreign Application Priority Data

Oct. 11, 2014    (CN) .......................... 2014 1 0532331

(51) Int. Cl.
| | | |
|---|---|---|
| *C07C 229/00* | (2006.01) | |
| *C07C 29/153* | (2006.01) | |
| *B01J 27/18* | (2006.01) | |
| *C07C 25/13* | (2006.01) | |
| *C07D 487/04* | (2006.01) | |
| *C07C 29/151* | (2006.01) | |

(52) U.S. Cl.
CPC ............. *C07C 29/153* (2013.01); *B01J 27/18* (2013.01); *C07C 25/13* (2013.01); *C07C 29/1514* (2013.01); *C07D 487/04* (2013.01); *B01J 2231/44* (2013.01); *B01J 2531/004* (2013.01)

(58) Field of Classification Search
CPC .................................................. C07C 29/153
USPC ....................................................... 560/47
See application file for complete search history.

(56) References Cited

FOREIGN PATENT DOCUMENTS

| CN | 102702205 A | * 10/2012 |
|---|---|---|
| CN | 103755596 A | 4/2014 |
| WO | 2005028419 A2 | 3/2005 |
| WO | 2009064476 A1 | 5/2009 |
| WO | WO-2009064476 A1 * | 5/2009 |

OTHER PUBLICATIONS

Matsumura, K. et al: "Practical, Catalytic Enantioselective Hydrogenation to Synthesize N-Unprotected beta-Amino Esters", Organic Process Research & Development, vol. 15, No. 5, Aug. 3, 2011, pp. 1130-1137 (Year: 2011).*
Matsumara, K., et al., "Practical, Catalytic Enantioselective Hydrogenation to Synthesize N-Unprotected beta-Amino Esters", Organic Process Reserach & Development, 15(5):1130-1137, Aug. 3, 2011.
EP150848178.8, Extended European Search Report, dated Dec. 19, 2017.

* cited by examiner

*Primary Examiner* — Deborah D Carr
(74) *Attorney, Agent, or Firm* — McCarter & English, LLP; Steven G. Davis; Wei Song

(57) ABSTRACT

Disclosed is a method for synthesizing a sitagliptin intermediate, the method comprising: in the presence of hydrogen and a transition metal catalyst having a chiral phosphine ligand, subjecting a compound of formula II to an asymmetric reductive amination with ammonia or ammonium salt in a proper organic solvent under the condition of adding an acidic additive to produce a compound of formula I, wherein, an R- or S-configuration of a stereocenter is represented by *; the compound of formula I of R configuration can be used to prepare sitagliptin, and a reaction formula is as follows: $R^1$ and $R^2$ are each independently selected from hydrogen, $C_1$-$C_{12}$ linear or branched alkyl, $C_3$-$C_{12}$ cycloalkyl, $C_2$-$C_{12}$ alkenyl, $C_2$-$C_{12}$ alkynyl and $C_7$-$C_{12}$ arylalkyl. The method has a high yield and a high ee % value, a mild reaction condition and a low production cost, and is simple to operate, convenient to purify, environmental friendly and suitable for industrial production.

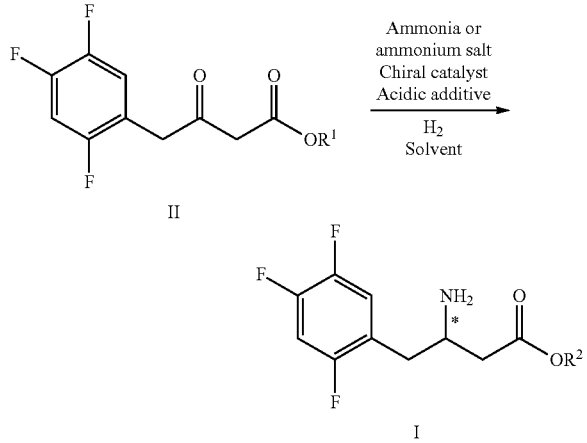

17 Claims, No Drawings

METHOD FOR PREPARING SITAGLIPTIN INTERMEDIATE VIA ASYMMETRICAL REDUCTION METHOD

CROSS-REFERENCE TO RELATED APPLICATIONS

The present application is a U.S. national stage application filed under 35 U.S.C. § 371(c), of International Application No. PCT/CN2015/091539, filed on Oct. 9, 2015, which claims the priority of Chinese Patent Application No. 201410532331.X, with the title of "METHOD FOR SYNTHESIZING SITAGLIPTIN INTERMEDIATE", filed with the State Intellectual Property Office of P.R.C on Oct. 11, 2014. The entire contents of each of the aforementioned applications are incorporated herein by reference.

TECHNICAL FIELD

The present invention relates to a method for preparing sitagliptin intermediate via asymmetric reduction.

BACKGROUND ART

Sitagliptin phosphate has a chemical name of 7-[(3R)-3-Amino-1-oxo-4-(2,4,5-trifluorophenyl)butyl]-5,6,7,8-tetrahydro-3-(trifluoromethyl)-1,2,4-triazolo[4,3-α]pyrazine phosphate, and the commercially medicine form is its monohydrate. The chemical structure thereof is shown as the following formula III:

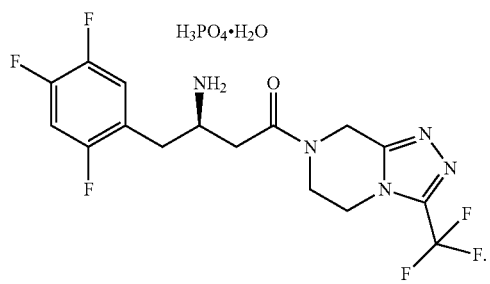

Sitagliptin phosphate is the first orally-effective and selective DPP-IV inhibitor on the market, and is used for treating Type II diabetes by oral administration once a day. Since launched to the market in 2006, sitagliptin phosphate has already entered about 60 countries, and more than 15 million prescription drugs have been made all over the world. The Phase III clinical trials of sitagliptin on treating Type I diabetes are in process. The trade name of sitagliptin phosphate tablet produced by Merck is JANUVIA (Sitagliptin Phosphate).

(R)-3-tert-butoxycarbonylamino-4-(2,4,5-trifluorophenyl)butanoic acid is one of the important intermediates for synthesizing sitagliptin, and the chemical structure thereof is shown as the following formula IV:

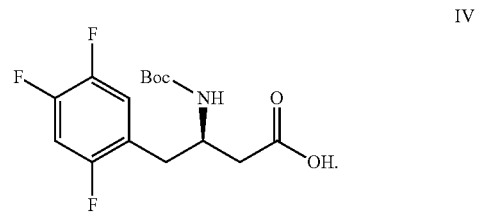 [SMILES: CC(C)(C)OC(=O)N[C@@H](CC(=O)O)Cc1cc(F)c(F)cc1F]

Based on comprehensive literature investigation, the inventors have found that the key step of synthesizing the compound of formula IV lies in constructing a chiral center of C3 attached to an amino group. Currently, the methods reported in the literatures are generally focusing on the step of preparing a proper substrate with trifluorophenylacetic acid as a start material and constructing a chiral center. There are mainly three methods: 1) separating racemates; 2) catalyzing a prochiral ketone with Ru-BINAP to obtain a chiral secondary alcohol, and reducing it after azidation; and 3) preparing an acyl-protected enamine, and subjecting it to asymmetric catalytic hydrogenation.

Method 1: PCT International Patent Publication WO2010009630 discloses a method in which racemate of β-amino acid intermediate F is separated and then converted to obtain compound IV. The specific synthesis route is shown as follows:.

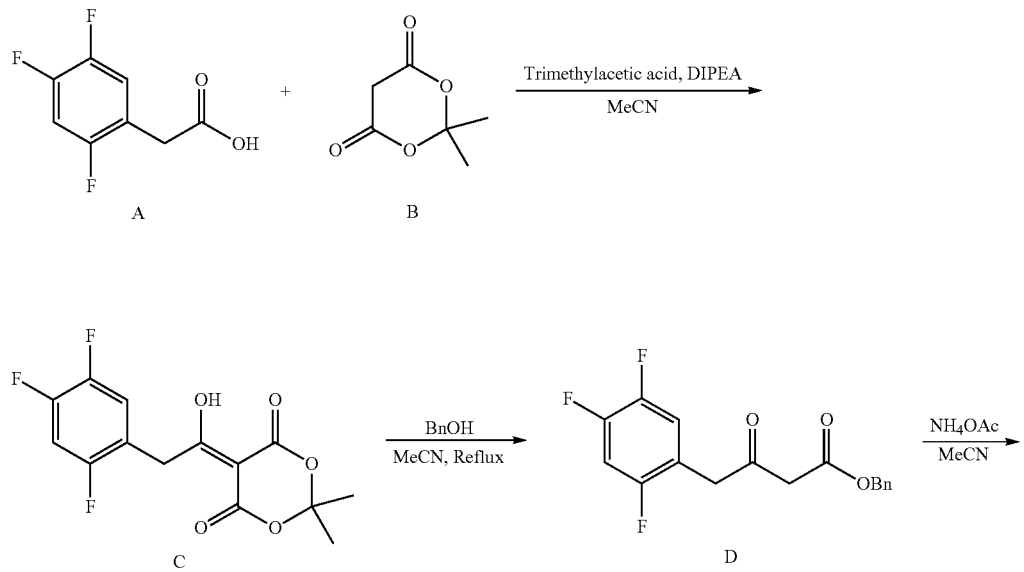

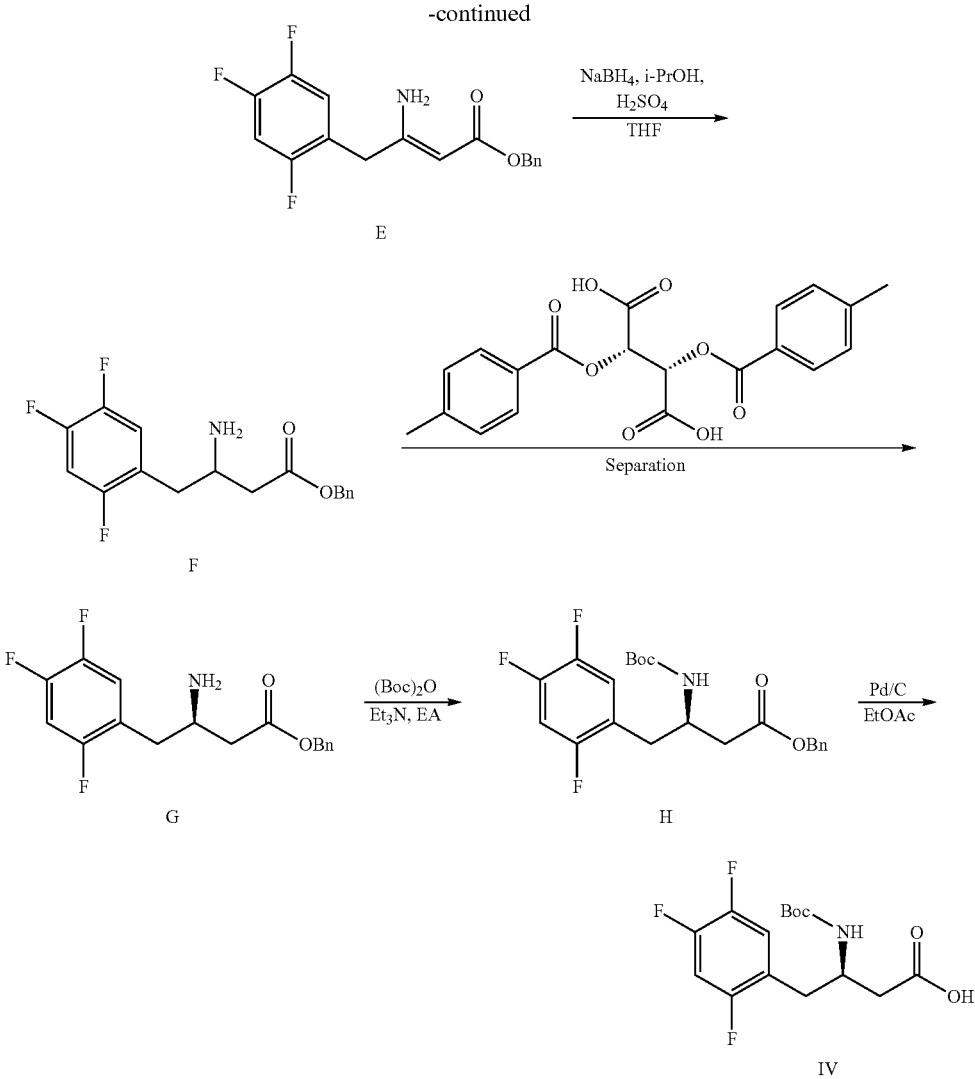

The main problems of this method are that:

1) in the reduction of the fourth step, the reaction starts only after borane is produced by catalyzing sodium borohydride with sulfuric acid; however, the use of sulfuric acid would increase the discharge of "three-waste" (waste gas, waste water and waste residues); further, borane gas is highly toxic, rendering potential safety risks; and 2) in the fifth step, a separation is required to obtain G, with a yield of about 31%; the yield is low, the economic efficiency is poor, and thus the production cost is significantly increased.

Method 2: PCT International Patent Publications WO2010122578, WO2004087650 and WO2009045507 each report methods for preparing a chiral alcohol through the asymmetric reduction of ketone intermediate with a chiral reductant (a chiral boron reagent, a chiral ruthenium and an enzyme, respectively). The chiral alcohol intermediate is then subjected to Mitsunobu reaction and the like to obtain compound IV. The specific synthesis route is shown as follows:

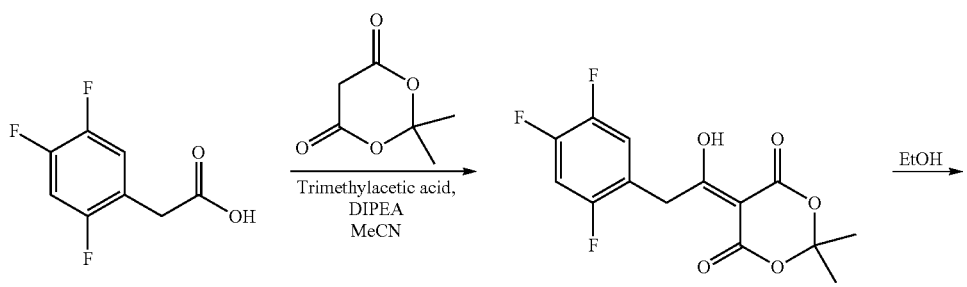

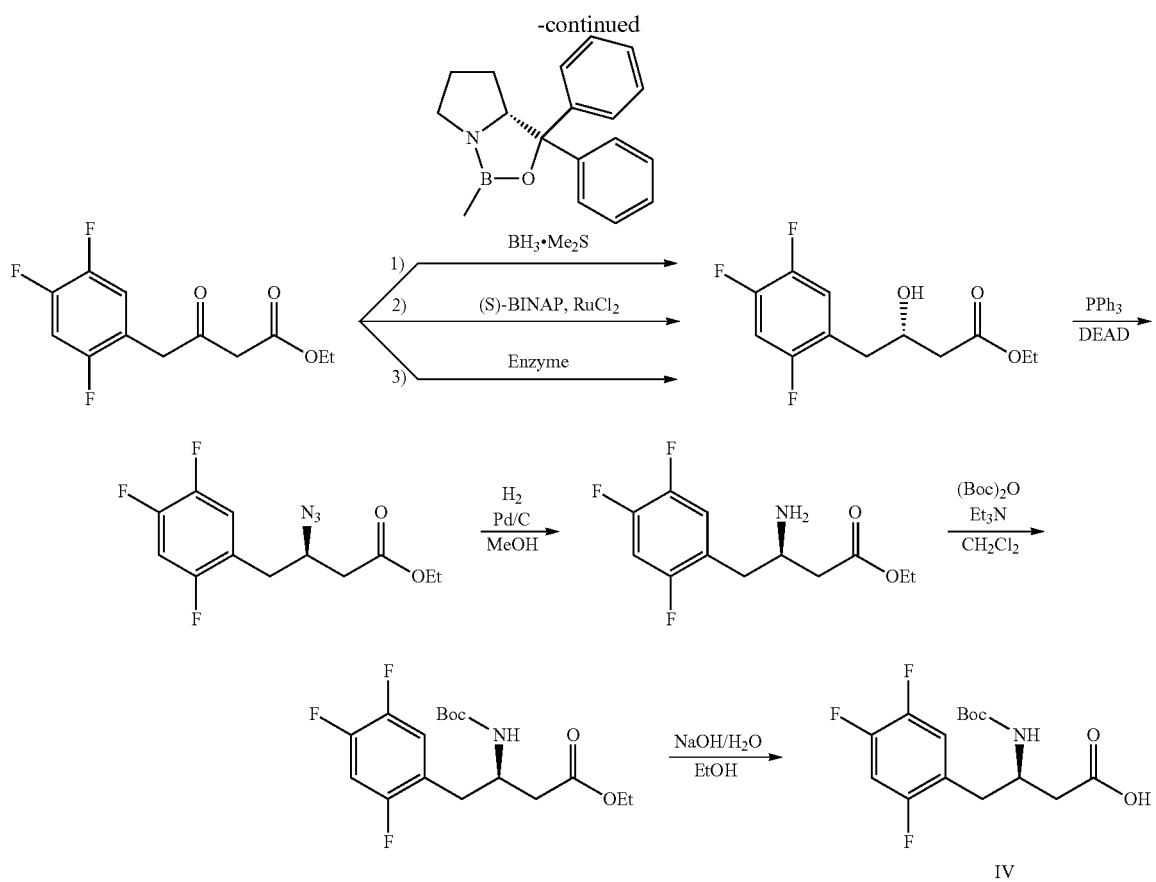

The main problems of this method are that:

1) in the reduction of the third step, the used (R)-Me-CBS catalyst is expensive, the borane reagent is highly toxic, and the enzyme is difficult to obtain;

2) in the fourth step, an azide is required, rendering large potential safety risks in scale-up production; and 3) seven steps of reactions are required to prepare compound IV, which is a long route.

Method 3: PCT International Patent Publications WO2009064476 and WO2010078440 each report methods for asymmetric catalytic hydrogenation of an enamine having a protecting group. The obtained intermediate can be used to prepare compound IV via suitable reactions. The specific synthesis route is shown as follows:

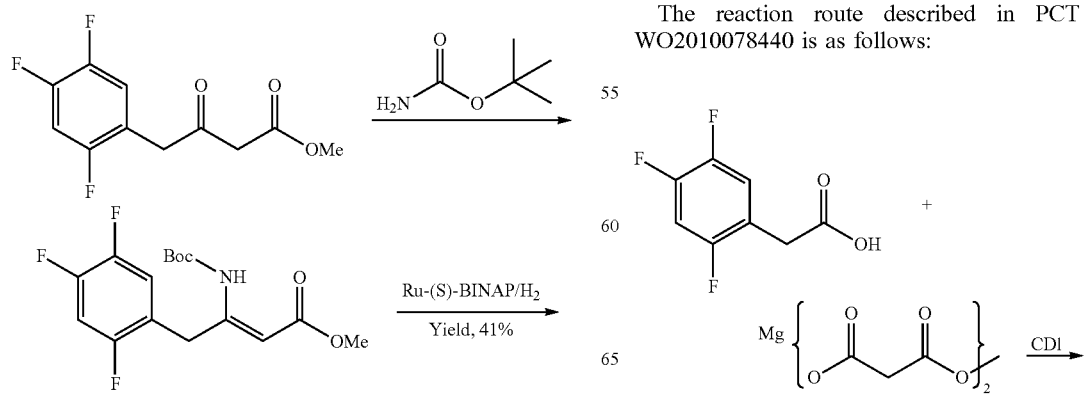

-continued

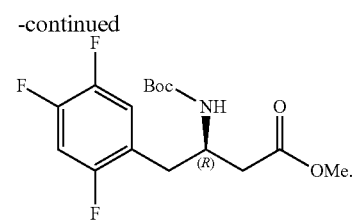

R:S = 66.2:33.8

The isomer purity in this method is low, and the yield is only 41%. Although 24% start materials can be recovered from the mother liquor, the cost and energy consumption is too high for industrial production.

The reaction route described in PCT Publication WO2010078440 is as follows:

-continued

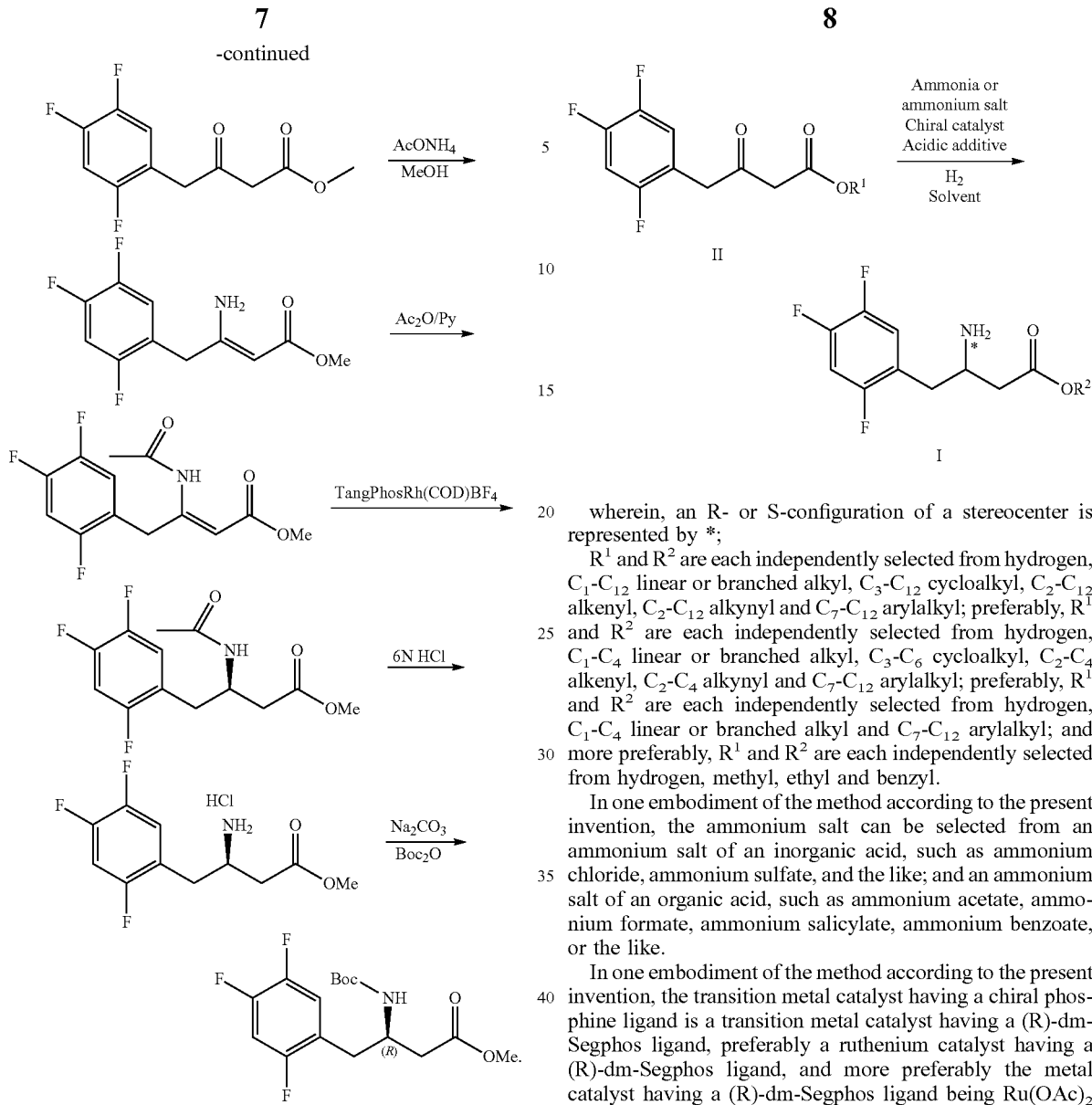

The main problems of this method are that: the asymmetric reduction proceeds only after the amino group of the enamine produced from the second step is protected. It is reported that the step of protecting the enamine results in a low yield.

SUMMARY OF THE INVENTION

The purpose of the present invention is to provide a new method for synthesizing an important intermediate compound for sitagliptin.

The technical solution of the present invention, in which asymmetric reductive amination is used to prepare the intermediate compound I, is as follows:

in the presence of hydrogen and a transition metal catalyst having a chiral phosphine ligand, subjecting a compound of formula II to an asymmetric reductive amination with ammonia or an ammonium salt in a proper organic solvent under the condition of adding an acidic additive to produce a sitagliptin intermediate of formula I, with the following reaction formula:

wherein, an R- or S-configuration of a stereocenter is represented by *;

$R^1$ and $R^2$ are each independently selected from hydrogen, $C_1$-$C_{12}$ linear or branched alkyl, $C_3$-$C_{12}$ cycloalkyl, $C_2$-$C_{12}$ alkenyl, $C_2$-$C_{12}$ alkynyl and $C_7$-$C_{12}$ arylalkyl; preferably, $R^1$ and $R^2$ are each independently selected from hydrogen, $C_1$-$C_4$ linear or branched alkyl, $C_3$-$C_6$ cycloalkyl, $C_2$-$C_4$ alkenyl, $C_2$-$C_4$ alkynyl and $C_7$-$C_{12}$ arylalkyl; preferably, $R^1$ and $R^2$ are each independently selected from hydrogen, $C_1$-$C_4$ linear or branched alkyl and $C_7$-$C_{12}$ arylalkyl; and more preferably, $R^1$ and $R^2$ are each independently selected from hydrogen, methyl, ethyl and benzyl.

In one embodiment of the method according to the present invention, the ammonium salt can be selected from an ammonium salt of an inorganic acid, such as ammonium chloride, ammonium sulfate, and the like; and an ammonium salt of an organic acid, such as ammonium acetate, ammonium formate, ammonium salicylate, ammonium benzoate, or the like.

In one embodiment of the method according to the present invention, the transition metal catalyst having a chiral phosphine ligand is a transition metal catalyst having a (R)-dm-Segphos ligand, preferably a ruthenium catalyst having a (R)-dm-Segphos ligand, and more preferably the metal catalyst having a (R)-dm-Segphos ligand being Ru(OAc)$_2$ ((R)-dm-Segphos), Ru(Cl)$_2$((R)-dm-Segphos) or the like.

In one embodiment of the method according to the present invention, the acidic additive can be an organic acid, preferably selected from salicylic acid, benzoic acid, tartaric acid, para-toluenesulfonic acid and the like. Notably, the purpose of adding the acidic additive into the reaction system is to obtain an acidic environment, and thus the acidic additive is not limited thereto. It is known to those skilled in the art that any acidic additive falls within the scope of the present invention as long as it can be used to achieve the purpose of the present invention and will not adversely affect the reaction of the present invention.

In one embodiment of the method according to the present invention, the used organic solvent can be alcohols, acetonitrile, toluene, N,N-dimethylformamide, 1,2-dichloroethane, ethyl acetate, dioxane, or the like. In one embodiment of the method according to the present invention, the alcohol is selected from methanol, ethanol, isopropanol, n-butanol, tert-butanol, benzyl alcohol, and the like, and preferably methanol, ethanol, and the like.

In one embodiment of the method according to the present invention, the pressure of hydrogen is preferably 2 to 10 MPa in the asymmetric reductive amination.

In one embodiment of the method according to the present invention, the temperature of the asymmetric reductive amination is preferably 50 to 100° C.

In one embodiment of the method according to the present invention, the mole percentage of the catalyst to the compound of formula II is 0.1 to 10.0 mol %, preferably 1 to 3 mol %.

The preferred technical solution of the present invention is as follows:

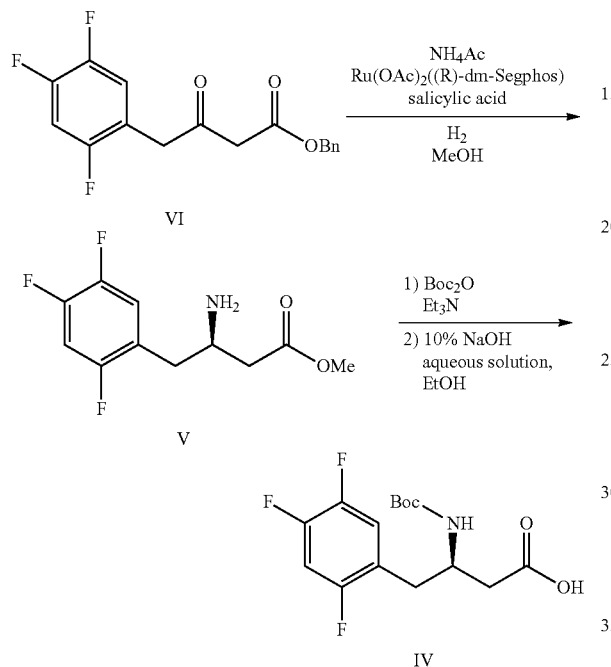

In the present invention, compound VI is subjected to an asymmetric reductive amination with ammonia or an ammonium salt (e.g. ammonium acetate) in the presence of Ru(OAc)$_2$((R)-dm-Segphos) and hydrogen with adding an acidic additive (e.g. salicylic acid) in a suitable organic solvent (e.g. methanol) to obtain compound V, and optionally compound V is protected by Boc and then hydrolyzed to prepare compound IV.

The advantageous technical effects of the present invention include: in the method for preparing sitagliptin intermediate via asymmetric reduction provided by the present invention, compound II can be directly subjected to an asymmetric reduction or subjected to a reductive amination with ammonia or an ammonium salt in the presence of a transition metal catalyst having a chiral phosphine ligand (for example, Ru(OAc)$_2$((R)-dm-Segphos)) in one single step to obtain compound I (ee %≥94%), without separation and amino-protection. Compound I is optionally protected by Boc and then hydrolyzed to prepare compound IV (ee %≥99%). Therein, if the reactant is compound VII, sitagliptin compound is obtained via the one-step asymmetric reduction. If the reactant has other substituents or heterocycle groups, the required sitagliptin intermediate compound can be obtained through selective amino-protection and then hydrolyzation of the reactant or direct hydrolyzation of the reactant. The asymmetric reduction provided by the present invention is a green synthesis method which has high atom utilization, short steps, high yield and ee % value, and is easy to operate, easy to purify, environment friendly and suitable for industry production.

DETAILED DESCRIPTION OF THE INVENTION

To better understand the purposes, technical features and effects of the present invention, the technical solutions of the present invention and the resulting technical effects thereof will be further explained below in combination with the examples.

Example 1: Preparation of Compound C

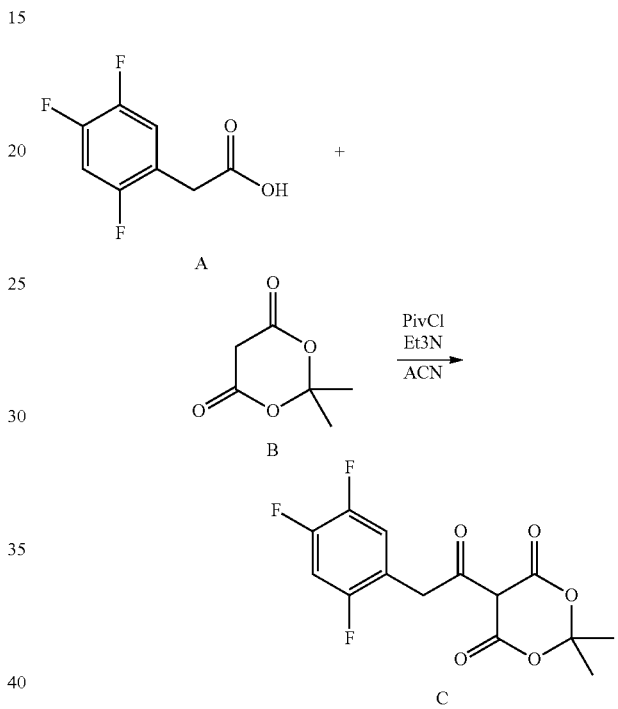

Under the protection of nitrogen, compound A (100 g, 0.524 mol), compound B (84 g, 0.583 mol), 4-dimethylaminopyridine (DMAP, 5.2 g, 0.042 mol) and acetonitrile (250 mL) were added sequentially into a 1000 mL three-necked flask, and were cooled to 0~5° C. While the temperature was kept at 0~30° C., triethylamine (150 mL, 1.079 mol) was added dropwise into the system. Then the system was cooled to 0~5° C. While the system was kept not higher than 30° C., pivaloyl chloride (76 mL, 1.17 mol) was added dropwise into the system. After the addition was completed, the system was heated to 40~45° C. The reaction was completed after 3~5 hours. Then, the system was cooled to 25~30° C. and filtrated. The filter cake was washed 2 times with 200 mL of methyl t-butyl ether. The solvent was evaporated (<30° C.) under reduced pressure to one fourth of the volume (in a sticky form), and then 600 mL of dichloromethane was added and stirred for 5 minutes (25~30° C.). About 300 mL of 1.5 M hydrochloric acid was added dropwise to the system over 15 minutes, adjusting pH=2~3. Then dichloromethane (DCM) phase was washed with 100 mL of NaCl saturated solution. The organic phase was evaporated (<15° C.) under reduced pressure to one third of the volume, and then 200 mL of n-heptane was added and then evaporated (<15° C.) under reduced pressure to one fourth of the volume. Then the system was supplemented with 50 mL of ethyl acetate and 300 mL of n-heptane and slurried for 2 hours. After suction filtration, the filter cake was washed with 100 mL of solvent (n-heptane:ethyl acetate=10:1) and then dried, obtaining 134.23 g of product, with a yield of 80.7%. ESI: m/z: 317 [M+H]$^+$.

Example 2: Preparation of Compound VI

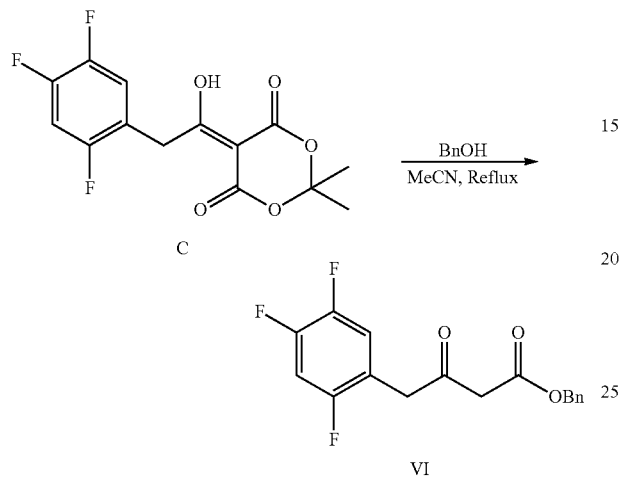

Under the protection of nitrogen, acetonitrile (284 mL), compound C (56.7 g, 0.179 mol), and benzyl alcohol (19.4 g, 0.179 mol) were added sequentially into a 250 mL three-necked flask, and then stirred. The system was heated to reflux for about 24 hours (inner temperature of 80~84° C. is a normal boiling point). The system was then cooled to not higher than 30° C., concentrated, and supplemented with methanol 3 times the volume of the system. The crystallization was conducted at 0~5° C. for 12 hours, followed by suction filtration, obtaining 47.2 g of product, with a yield of 81.6%. $^1$H NMR (400 MHz, CDCl$_3$) δ: 7.37-7.35 (m, 5H), 6.99-6.89 (m, 2H), 5.19 (s, 2H), 3.81 (s, 2H), 3.57 (s, 2H); ESI: m/z: 323 [M+H]$^+$.

Example 3: Preparation of Compound V

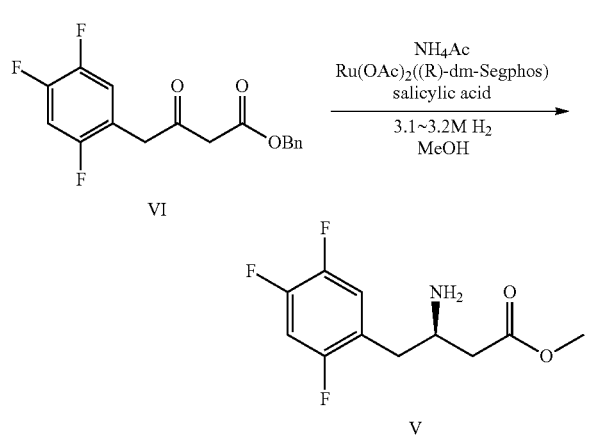

Compound VI (100 g, 0.310 mol), salicylic acid (214 g, 0.898 mol), ammonium acetate (119 g, 1.544 mol), chiral catalyst Ru(OAc)$_2$((R)-dm-Segphos) (2.93 g, 0.003 mol) and methanol (400 mL) were added into a 1000 mL hydrogenation reactor. The system was subjected to nitrogen replacement for 5 times, and to hydrogen replacement for 3 times, and then supplemented with hydrogen to the pressure of 2.5 MPa. The temperature was increased to 40~50° C., and the pressure was increased to 2.7 MPa. Subsequently, hydrogen was added to the pressure of 3.6 MPa. The temperature was increased to 70~80° C., and the pressure was 3.6 MPa. The reaction was conducted at a constant temperature. The reaction was monitored with TLC, and completed after about 20 hours. Then the heating was stopped, and the system was cooled to the room temperature. Hydrogen was discharged, and the system was subjected to nitrogen replacement for 3 times, followed by suction filtration of the reaction solution. The resulting filtrate was concentrated, supplemented with 200 mL of sodium carbonate solution, and then extracted with ethyl acetate for 2 times (300 mL×2). The organic phase was concentrated, obtaining 72.96 g of product, with a yield of 95.2% and ee % of 94.2%. $^1$H NMR (400 MHz, CDCl$_3$) δ: 7.26-7.09 (m, 1H), 6.94-6.89 (m, 1H), 3.71 (s, 3H), 3.59-3.49 (m, 1H), 2.84-2.83 (m, 3H), 2.61-2.45 (m, 3H); ESI: m/z: 248 [M+H]$^+$.

Example 4: Preparation of Compound V

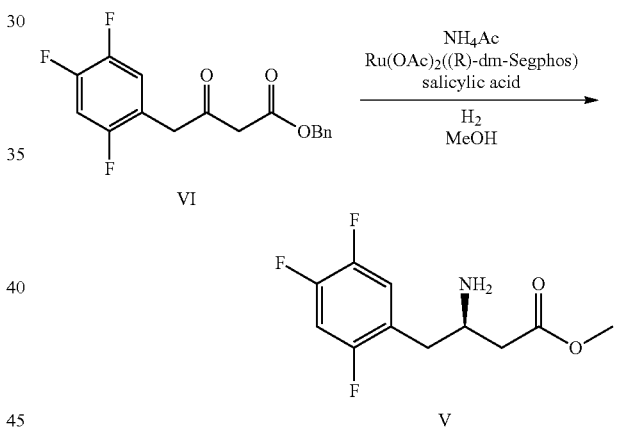

Compound VI (100 g, 0.310 mol), salicylic acid (214 g, 0.898 mol), ammonium acetate (119 g, 1.544 mol), chiral catalyst Ru(OAc)$_2$((R)-dm-Segphos) (2.93 g, 0.003 mol) and methanol (400 mL) were added into a 1000 mL hydrogenation reactor. The system was subjected to nitrogen replacement for 5 times, and to hydrogen replacement for 3 times, and then supplemented with hydrogen to the pressure of 2.0 MPa. The temperature was increased to 90~100° C. The reaction was conducted at a constant temperature. The reaction was monitored with TLC, and completed after about 20 hours. Then the heating was stopped, and the system was cooled to the room temperature. Hydrogen was discharged, and the system was subjected to nitrogen replacement for 3 times, followed by suction filtration of the reaction solution. The resulting filtrate was concentrated, supplemented with 200 mL of sodium carbonate solution, and then extracted with ethyl acetate for 2 times (300 mL×2). The organic phase was concentrated, obtaining 67.85 g of product, with a yield of 88.5%. ESI: m/z: 248 [M+H]$^+$.

Example 5: Preparation of Compound V

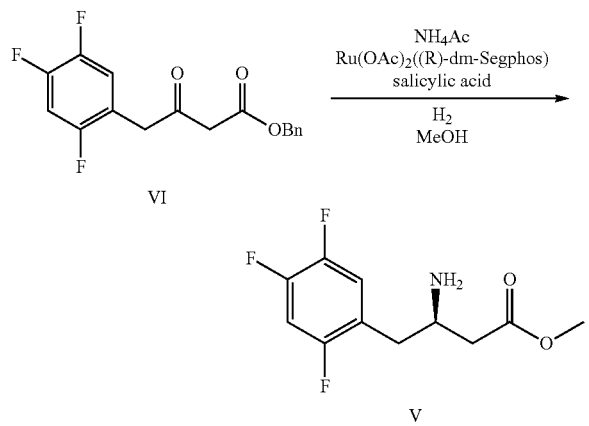

Compound VI (100 g, 0.310 mol), salicylic acid (214 g, 0.898 mol), ammonium acetate (119 g, 1.544 mol), chiral catalyst Ru(OAc)$_2$((R)-dm-Segphos) (2.93 g, 1 mol %) and methanol (400 mL) were added into a 1000 mL hydrogenation reactor. The system was subjected to nitrogen replacement for 5 times, and to hydrogen replacement for 3 times, and then supplemented with hydrogen to the pressure of 9~10 MPa. The temperature was increased to 40~50° C. The reaction was conducted at the constant temperature. The reaction was monitored with TLC, and completed after about 12 hours. Then the heating was stopped, and the system was cooled to the room temperature. Hydrogen was discharged, and the system was subjected to nitrogen replacement for 3 times, followed by suction filtration of the reaction solution. The resulting filtrate was concentrated, supplemented with 200 mL of sodium carbonate solution, and then extracted with ethyl acetate for 2 times (300 mL×2). The organic phase was concentrated, obtaining 73.82 g of product, with a yield of 96.3%. ESI: m/z: 248 [M+H]$^+$.

Example 6: Preparation of Compound IV

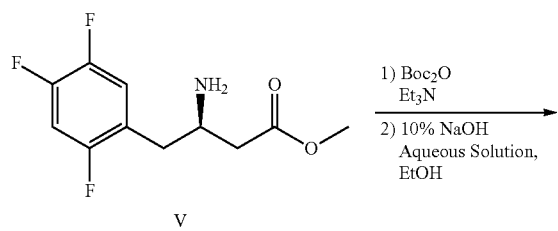

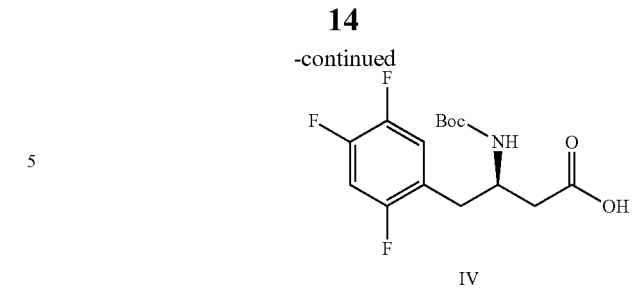

Compound V (32.0 g, 0.129 mol), di-tert-butyl dicarbonate ((Boc)$_2$O 29.5 g, 0.135 mol) and triethylamine (21.2 g, 0.210 mol) were dissolved in ethyl acetate (150 mL). The reaction was conducted at a controlled temperature of 20~30° C. The reaction was monitored with TLC, and completed after 7 hours. 10 mL of water was added to wash the system, and the organic phase was concentrated to obtain a crude product. The crude product was dissolved in ethanol, and supplemented with 10% sodium hydroxide aqueous solution. The reaction was conducted at a controlled temperature of 20~30° C. for 2 hours. The reaction was monitored with TLC. After the completion of the reaction, the system was supplemented with 30 mL of water, and the pH was adjusted to 1~2 with 3M hydrochloric acid. A large amount of solids were precipitated, suction filtrated, and dried, obtaining 36.8 g of product, with a yield of 85.5% and ee % of 99.3%. [a]=+32.3 (c 1.0, CHCl$_3$); $^1$H NMR (400 MHz, CDCl$_3$) δ: 7.26-7.03 (m, 1H), 6.94-6.88 (m, 1H), 5.08 (d, J=9.6 Hz, 1H), 4.15 (br, 1H), 2.89 (d, J=7.2 Hz, 1H), 2.63 (d, J=5.2 Hz, 1H), 1.38 (s, 9H); ESI: m/z: 233 [M-Boc]$^+$, 356[M+Na]$^+$.

Examples 7-10

Compound II was prepared in a similar way with that of Example 2. The results are as shown in Table 1 below.

TABLE 1

| Example No. | Reactant 1 | Reactant 2 | R$^1$ in compound II | Yield |
|---|---|---|---|---|
| 7 | Compound C | Methanol | Methyl | 83.1% |
| 8 | Compound C | Ethanol | Ethyl | 80.3% |
| 9 | Compound C | Isopropanol | Isopropyl | 82.4% |
| 10 | Compound C | Tert-butanol | Tert-butyl | 79.7% |

Examples 11-18

Compound I was prepared in a similar way with that of Examples 3-5. The results are as shown in Table 2 below.

TABLE 2

| Example No. | R$^1$ in compound II | Acidic additive | Amination reagent | Catalyst | Ratio of catalyst (mol %) | Solvent | Hydrogen Pressure (MPa) | Reaction temperture (° C.) | R$^2$ in compound I | ee % | Yield |
|---|---|---|---|---|---|---|---|---|---|---|---|
| 11 | Methyl | Salicylic acid | Ammonium acetate | Ru(OAc)$_2$((R)-dm-Segphos) | 0.1 | Methanol | 2.0 | 60 | Methyl | 96.7 | 95.2% |
| 12 | Ethyl | Salicylic acid | Ammonium acetate | Ru(Cl)$_2$((R)-dm-Segphos) | 0.5 | Methanol | 4.0 | 60 | Methyl | 95.3 | 93.5% |
| 13 | Benzyl | Tartaric acid | Ammonium sulfate | Ru(OAc)$_2$((R)-dm-Segphos) | 2 | Ethanol | 6.0 | 60 | Ethyl | 88.6 | 69.6% |

TABLE 2-continued

| Example No. | $R^1$ in compound II | Acidic additive | Amination reagent | Catalyst | Ratio of catalyst (mol %) | Solvent | Hydrogen Pressure (MPa) | Reaction temperture (° C.) | $R^2$ in compound I | ee % | Yield |
|---|---|---|---|---|---|---|---|---|---|---|---|
| 14 | Benzyl | Benzoic acid | Ammonium formate | Ru(OAc)$_2$((R)-dm-Segphos) | 5 | Benzyl alcohol | 6.5 | 70 | Benzyl | 89.3 | 76.2% |
| 15 | Methyl | p-toluene-sulfonic acid | Ammonium salicylate | Ru(Cl)$_2$((R)-dm-Segphos) | 5 | Acetonitrile | 7.1 | 70 | Methyl | 93.2 | 83.5% |
| 16 | Methyl | Salicylic acid | Ammonium benzoate | Ru(OAc)$_2$((R)-dm-Segphos) | 7 | Toluene | 8.3 | 80 | Methyl | 89.7 | 70.1% |
| 17 | Benzyl | Salicylic acid | Ammonium acetate | Ru(OAc)$_2$((R)-dm-Segphos) | 5 | DMF | 5.0 | 90 | Benzyl | 93.2 | 67.4% |
| 18 | Methyl | Salicylic acid | Ammonium formate | Ru(Cl)$_2$((R)-dm-Segphos) | 8 | DCE | 10.0 | 100 | Methyl | 81.9 | 62.3% |

Examples 19-21

In a similar way with that of Example 6, compounds I prepared in Example 11-18 were respectively hydrolysed to obtain compound IV. The results are as shown in Table 3 below.

TABLE 3

| Example No. | $R^2$ in compound I | ee % | Yield |
|---|---|---|---|
| 19 | Ethyl | 99.2% | 82.3% |
| 20 | Benzyl | 99.6% | 84.1% |
| 21 | Tert-butyl | 99.5% | 82.7% |

The description above only provides preferred examples of the present invention, but is not intended to limit the present invention. Any modification, equivalent replacement, and improvement within the spirit and principle of the present invention should be included within the scope of the present invention.

The invention claimed is:

1. A method for synthesizing sitagliptin intermediate represented by formula I via asymmetric reduction, characterized in that, it comprises the following steps: in the presence of hydrogen and a transition metal catalyst having a chiral phosphine ligand, subjecting a compound of formula II to an asymmetric reductive amination with ammonia or an ammonium salt in a proper organic solvent under the condition of adding an acidic additive to produce sitagliptin intermediate of formula I, with the following reaction formula:

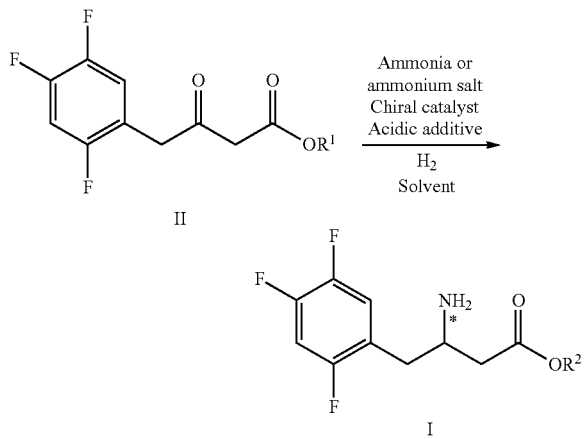

wherein, an R- or S-configuration of a stereocenter is represented by *; and $R^1$ and $R^2$ are each independently selected from hydrogen, $C_1$-$C_{12}$ linear or branched alkyl, $C_3$-$C_{12}$ cycloalkyl, $C_2$-$C_{12}$ alkenyl, $C_2$-$C_{12}$ alkynyl and $C_7$-$C_{12}$ arylalkyl; and wherein the acidic additive is an organic acid selected from salicylic acid, tartaric acid, p-toluenesulfonic acid, or a combination thereof.

2. The method according to claim 1, characterized in that, $R^1$ and $R^2$ are each independently selected from hydrogen, $C_1$-$C_4$ linear or branched alkyl, $C_3$-$C_6$ cycloalkyl, $C_2$-$C_4$ alkenyl, $C_2$-$C_4$ alkynyl and $C_7$-$C_{12}$ arylalkyl.

3. The method according to claim 1, characterized in that, the transition metal catalyst having a chiral phosphine ligand is a transition metal catalyst having a (R)-dm-Segphos ligand.

4. The method according to claim 1, characterized in that, the ammonium salt is selected from an ammonium salt of an inorganic acid or an ammonium salt of an organic acid.

5. The method according to claim 4, characterized in that, the ammonium salt of an inorganic acid is selected from ammonium chloride, ammonium sulfate, or a combination thereof; and the ammonium salt of an organic acid is selected from ammonium acetate, ammonium formate, ammonium salicylate, ammonium benzoate, or a combination thereof.

6. The method according to claim 1, characterized in that, the organic solvent is selected from alcohols, acetonitrile, toluene, N,N-dimethylformamide, 1,2-dichloroethane, or a combination thereof.

7. The method according to claim 1, characterized in that, the organic solvent is selected from alcohols, and the alcohols are selected from methanol, ethanol, isopropanol, n-butanol, tert-butanol, benzyl alcohol, or a combination thereof.

8. The method according to claim 1, characterized in that, the mole percentage of the catalyst to the compound of formula II is 0.1 to 10.0 mol %.

9. The method according to claim 1, characterized in that, the hydrogen pressure is 2 to 10 MPa in the asymmetric reductive amination.

10. The method according to claim 1, characterized in that, the temperature of the asymmetric reductive amination is 50 to 100° C.

11. The method according to claim 2, characterized in that, $R^1$ and $R^2$ are each independently selected from hydrogen, $C_1$-$C_4$ linear or branched alkyl and $C_7$-$C_{12}$ arylalkyl.

12. The method according to claim 2, characterized in that, $R^1$ and $R^2$ are each independently selected from hydrogen, methyl, ethyl and benzyl.

13. The method according to claim 3, characterized in that, the transition metal catalyst having a chiral phosphine ligand is a ruthenium catalyst having a (R)-dm-Segphos ligand.

14. The method according to claim 3, characterized in that, the transition metal catalyst having a chiral phosphine ligand is selected from Ru(OAc)$_2$((R)-dm-Segphos) and/or Ru(Cl)$_2$((R)-dm-Segphos).

15. The method according to claim 7, characterized in that, the alcohols are selected from methanol, ethanol, or a combination thereof.

16. The method according to claim 8, characterized in that, the mole percentage of the catalyst to the compound of formula II is 1 to 3 mol %.

17. A method for synthesizing sitagliptin, comprising the following steps:
  a) synthesizing sitagliptin intermediate represented by formula I with the method according to claim 1, and
  b) converting the sitagliptin intermediate obtained in step a) to sitagliptin.

* * * * *